United States Patent
Siewert et al.

(10) Patent No.: US 10,328,405 B2
(45) Date of Patent: Jun. 25, 2019

(54) PROCESS FOR THE PRODUCTION OF SOLID COOLING AGENTS

(71) Applicant: Symrise AG, Holzminden (DE)

(72) Inventors: Jürgen Siewert, Rollshausen (DE); Michael Michler, Eimen (DE); Jörg Niekerken, Holzminden (DE); Oliver Lenz, Uslar (DE); Christian Wolter, Ottenstein (DE)

(73) Assignee: Symrise AG, Holzminden (DE)

( * ) Notice: Subject to any disclaimer, the term of this patent is extended or adjusted under 35 U.S.C. 154(b) by 16 days.

(21) Appl. No.: 15/329,457

(22) PCT Filed: Jul. 26, 2015

(86) PCT No.: PCT/EP2015/067093
§ 371 (c)(1),
(2) Date: Jan. 26, 2017

(87) PCT Pub. No.: WO2016/016154
PCT Pub. Date: Feb. 4, 2016

(65) Prior Publication Data
US 2017/0216802 A1 Aug. 3, 2017

(30) Foreign Application Priority Data
Jul. 29, 2014 (EP) .................... 14179023

(51) Int. Cl.
*B01J 2/26* (2006.01)
*A61K 47/12* (2006.01)
*A61K 9/20* (2006.01)

(52) U.S. Cl.
CPC ............ *B01J 2/26* (2013.01); *A61K 9/2013* (2013.01); *A61K 47/12* (2013.01)

(58) Field of Classification Search
CPC ................... C07C 35/12; B01J 2/26
See application file for complete search history.

(56) References Cited

U.S. PATENT DOCUMENTS

| | | | |
|---|---|---|---|
| 3,023,253 A | 2/1962 | Bain et al. | |
| 3,064,311 A | 11/1962 | Bain et al. | |
| 5,013,498 A * | 5/1991 | Froeschke | A23G 3/0252 264/164 |
| 2006/0279947 A1* | 12/2006 | Henley, Jr. | F25D 27/00 362/154 |
| 2010/0185024 A1* | 7/2010 | Rauls | B01J 2/24 568/840 |

FOREIGN PATENT DOCUMENTS

| | | |
|---|---|---|
| WO | 03/101924 A1 | 12/2003 |
| WO | 2007/071512 A1 | 6/2007 |
| WO | 2008/152009 A1 | 12/2008 |
| WO | 2010/095304 A1 | 8/2010 |

* cited by examiner

*Primary Examiner* — Alexandre F Ferre
(74) *Attorney, Agent, or Firm* — Dilworth & Barrese, LLP

(57) ABSTRACT

Suggested is a process for the production of solid cooling agents, wherein a pre-scraped melt, i.e., a melt of menthol compounds with added seed crystals is applied to a pre-cooled area by even deposition of drops.

7 Claims, 2 Drawing Sheets

Pastilles of example 1

Pastilles of example 2

Pastilles of example 3

Pastilles of example 4

Pastilles of example 5

Test set up

PROCESS FOR THE PRODUCTION OF SOLID COOLING AGENTS

FIELD OF THE INVENTION

The invention is in the field of cooling agents, specifically of menthol and menthol compounds, and relates to a process for the production of corresponding solid cooling agents, particularly of flakes or pastilles with improved storage properties and a reduced tendency to sublime.

STATE OF THE ART

Menthol is an agent occurring in nature, which causes a cooling effect when brought in contact with mucous membranes, specifically the oral mucosa. Menthol and numerous subsequently developed menthol compounds with an, in part, significantly increased cooling effect are thus widely used in the pharmaceutical, cosmetic and food industries. Menthol is found in natural sources, for example, in peppermint oil, in the form of four diastereomeric pairs of enantiomers of which only the main component, (−)-menthol or L-menthol, has the desired taste and other sensory properties, as already described in J. Am. Chem. Soc, Vol. 39 (8), 1917, pp. 1515-1525. Particularly the melting points of these various forms are between 33 and 43° C., as described in Archiv der Pharmazie, 307 (7), 1974, pp 497-503. Accordingly, the melting point of the stable α-form is between 42 and 43° C.

Due to this situation of the melting points, L-menthol and most menthol compounds can be administered to the end user both as a melt that is kept liquid in heated containers and also in the form of crystals or other congealed molded bodies such as granular materials, pastilles, flakes and the like. Generally, all solids which have a melting point of barely above the ambient temperature such as L-menthol and the substances that are structurally related to menthol have a strong tendency to cake and to agglomerate. The processing of such material that does not comply with the specification, however, involves a substantial additional effort. If pure L-menthol or menthol compounds is to be sold as a solid, i.e., material that has not been treated with additives such as, for example, separating agents, it must be ensured that the product will reach the end user in pourable form, either by an unbroken cold chain or by the way of shaping.

Menthol is commercially available, for example, in the form of large crystals having a thickness of from 1 to 3 mm at a length of from 0.5 to 3 cm. They are traditionally grown in small amounts from naturally obtained peppermint oil, where the oil is allowed to crystallise in troughs or tubs in cold storage for many days. These crystals have a ready pourability at a low filling height only, but they increasingly agglomerate visibly at an increased load and/or an increased temperature. The technical effort to realize the crystallisation, the separation and the purification of the crystals and the low space/time profit of such a long-term process render it unattractive for industrial use.

DE 2530481 relates to a device for the crystallising of substances, particularly of optically active menthol compounds which under crystallisation conditions form coarse needle- or bar-shaped crystals. The crystallisation process that is to be carried out discontinuously is performed by means of a particular stirrer that prevents an agglomeration of the crystals in the crystal suspension. The valuable product is eventually isolated by a centrifuge and dried in a dryer.

The two patent specifications U.S. Pat. Nos. 3,023,253 and 3,064,311 describe flaked L-menthol and a process for the preparation of such flakes by applying a melt of L-menthol onto a cooled pan roller; however, these mixtures do not contain any seed crystals. If desired, the menthol melt may be introduced between a pair of counter-rotating, cooled rollers. The menthol film that has begun to crystallise on the pan roller is post-processed by tempering it by means of an introduction of heat, and reinforced by applying additional menthol. Both post-treatments are obtained simultaneously by means of a feed roller. Initially, the flakes such obtained exhibit a good pourability. After longer storage, however, a slight caking takes place that requires a mechanical loosening by shaking the container. It is noted that this caking is caused by a porous surface that is mentioned but not characterised in more detail and an accompanying heavy sublimation of the product, and that the product such obtained may be further processed to pellets by compacting.

The principle of further enlargement of the primary particles by compacting is also described in DE 10224087, relating to compacted menthol in the form of menthol pellets as well as a process for the production thereof. Here, however, the focus is not on the effect of the particle size alone, but on the fact that the primary particles must be present in a specific crystal form. On condition that these predominantly consist of the thermodynamically stable α-form that only melts at 42.5° C., it is possible to obtain granular materials that are resistant against caking by compressing crystals obtained from solution crystallisation or from the formation of flakes on cooling rollers.

The subject-matter of the international patent application WO 2008 152009 A1 (BASF) is a process for the production of L-menthol in solid form by bringing an L-menthol melt into contact with two cooled surfaces that are spaced apart from one another while the L-menthol melt is congealing, resulting in L-menthol in solid form, whereby the contact between the congealing L-menthol melt and the cooled surfaces is maintained at least until congelation is completed. In this process, the crystallisation of menthol is effected by a combination of a pre-crystalliser and a double-belt cooler. Herein, the menthol suspension is introduced into the gap between two cooled surfaces and allowed to congeal or crystallize.

The processes of the state of the art share a number of serious disadvantages, namely, particularly, a low storage stability. Directly after storing, the products start to agglomerate, needles are formed as a result of sublimation, the crystals break as a result of insufficient mechanical solidity, so that, in sum, the product according to the specification is not obtained, which gives rise to various complaints.

The object of the present invention was, therefore, to provide solid cooling agents, particularly, menthol pastilles, exhibiting a significantly lower tendency to agglomerate and, particularly, being less prone to break easily. At the same time, the process should be carried out such that there is as little caking as possible during cooling and thus only little product loss. Eventually, the granular materials or pastilles such obtained are intended to emit as little residual heat as possible.

DESCRIPTION OF THE INVENTION

The subject-matter of the invention is a process for the production of solid cooling agents in which a pre-scraped melt, i.e., a melt of menthol compounds with added seed crystals is placed onto a pre-cooled area by even deposition of drops.

Surprisingly, it was found that the solid cooling agents obtainable according to the process of the invention, specifically, the pastilles, in contrast to the state of the art
 (a) do not agglomerate during storage and transport and have a visibly smaller portion of broken particles;
 (b) leave significantly less caking on the cooling belt;
 (c) have a significantly lower proportion of fines and thus provide a higher yield;
 (d) in addition, have curved surfaces, thus having only few contact points with one another when poured;
 (e) have a surface-to-volume ratio, as a result of which the tendency to sublime is further reduced;
 (f) have a smaller tendency to form bridges (low solidification during storage);
 (g) emit a low amount of residual heat in the packaging.

BRIEF DESCRIPTION OF THE DRAWINGS

The present invention will be described in greater detail with reference to the accompanying drawings, in which.

Menthol and Methol Compounds

Figure 1:
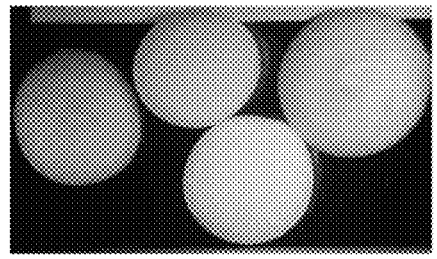
FIG. 1 is a photograph of pastilles prepared according to Example 1 of the present invention.

Menthol compounds which can be applied within the meaning of the invention are—besides the basic structure of menthol itself—products to be solidified, for example, selected from the group consisting of Menthol Methyl Ether, Menthone Glyceryl Acetal (FEMA GRAS[1] 3807), Menthone Glyceryl Ketal (FEMA GRAS 3808), Menthyl Lactate (FEMA GRAS 3748), Menthol Ethylene Glycol Carbonate (FEMA GRAS 3805), Menthol Propylene Glycol Carbonate (FEMA GRAS 3806), Menthyl-N-ethyloxamate, Monomethyl Succinate (FEMA GRAS 3810), Monomenthyl Glutamate (FEMA GRAS 4006), Menthoxy-1,2-propanediol (FEMA GRAS 3784), Menthoxy-2-methyl-1,2-propanediol (FEMA GRAS 3849) as well as the menthane carboxylic esters and amides WS-3, WS-4, WS-5, WS-12, WS-14 and WS-30 and their mixtures.

[1] FEMA stands for "Flavor and Extracts Manufacturers Association", and GRAS is defined as "Generally Regarded As Safe". A FEMA GRAS designation means that the substance marked as such has been tested according to standard methods and is considered to be toxicologically safe.

A first important representative of the cooling agents is Monomenthyl Succinate (FEMA GRAS 3810), which has been patented as a substance by Brown & Williamson Tobacco Corp. (U.S. Pat. No. 3,111,127) already in 1963, and as a cooling agent, which is the subject-matter of the industrial property rights U.S. Pat. Nos. 5,725,865 and 5,843,466 (V.Mane Fils). Both the succinate and also the analogous Monomenthyl Glutarate (FEMA GRAS 4006) are important representatives of monomenthyl esters on the basis of di- and polycarboxylic acids:

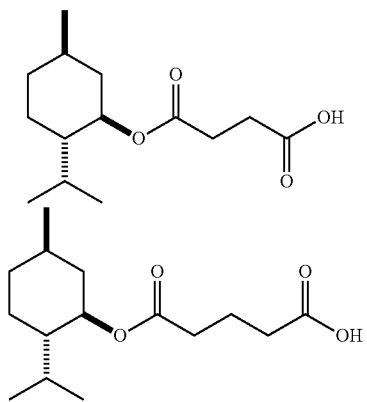

Examples of applications of these substances can be found, for example, in the patent specifications WO 2003 043431 (Unilever) or EP 1332772 A1 (IFF).

The next important group of preferred menthol compounds within the meaning of the invention comprises carbonate esters of menthol and polyols such as, for example, glycols, glycerol or carbohydrates such as, for example, Menthol Ethylene Glycol Carbonate (FEMA GRAS 3805=Frescolat® MGC), Menthol Propylene Glycol Carbonate (FEMA GRAS 3784=Frescolat® MPC), Menthol 2-Methyl-1,2-propanediol Carbonate (FEMA GRAS 3849) or the respective sugar derivatives:

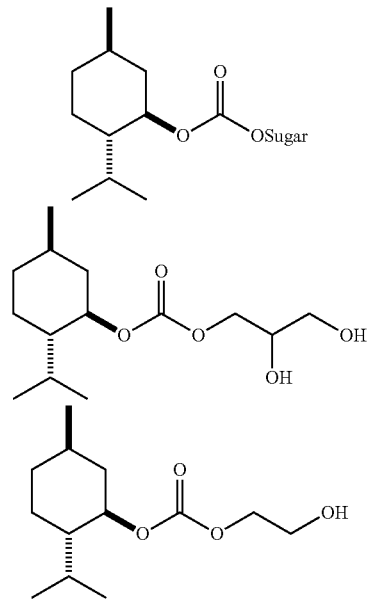

Menthol ethylene glycol carbonate

The use of such substances as cooling agent for cigarettes is, for example, the subject matter of the patent specification U.S. Pat. No. 3,419,543 (Mold et al.) of the year 1968; its use as physiological cooling substance is claimed in DE 4226043 A1 (H&R).

The menthol compounds Menthyl Lactate (FEMA GRAS 3748=Frescolat® ML) and, particularly, Menthone Glyceryl Acetal (FEMA GRAS 3807) or Menthone Glyceryl Ketal (FEMA GRAS 3808) which is marketed under the designation Frescolat® MAG are preferred within the meaning of the invention.

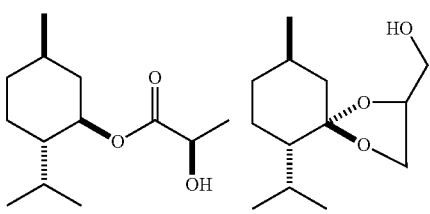

The former structure is obtained by esterification of lactic acid with menthol, the latter by acetalisation of menthone with glycerol (cf. DE 2608226 A1, H&R). This group of compounds also includes 3-(1-Menthoxy)-1,2,propanediol, which is also known as Cooling Agent 10 (FEMA GRAS 3784, vgl. U.S. Pat. No. 6,328,982, TIC), and 3-(I-Menthoxy)-2-methyl-1,2,propanediol (FEMA GRAS 3849), which has an additional methyl group.

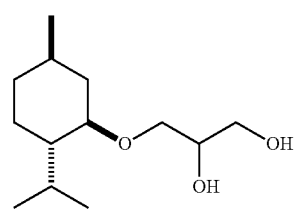

Cooling Agent 10

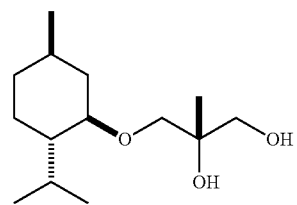

I-Menthoxy-2-methyl 1, 2-propanediol

The production of 3-(I-Menthoxy)-1,2,propanediol is carried out, for example, on the basis of menthol according to the following scheme (cf. U.S. Pat. No. 4,459,425, Takagaso):

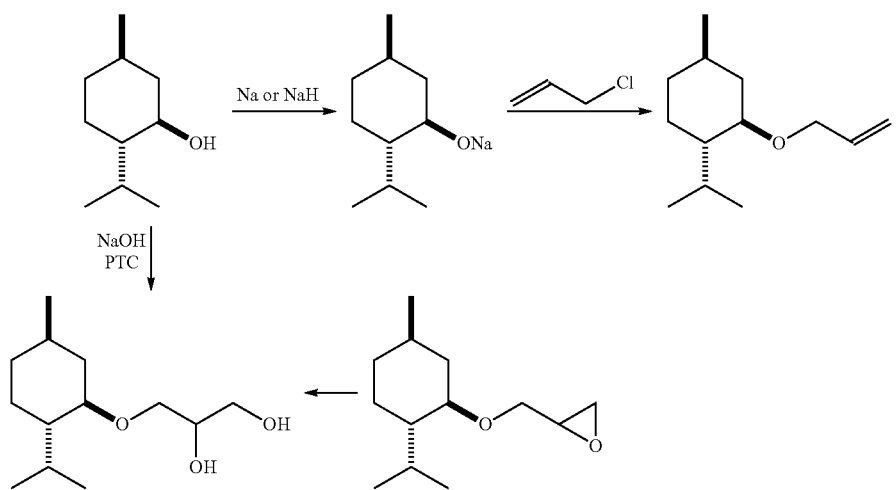

Alternative routes, in which menthol is reacted with epichlorohydrin in the first step, are described in U.S. Pat. Nos. 6,407,293 and 6,515,188 (Takagaso). In the following, an overview is provided of the preferred menthol compounds which are characterized by a C—O bond:

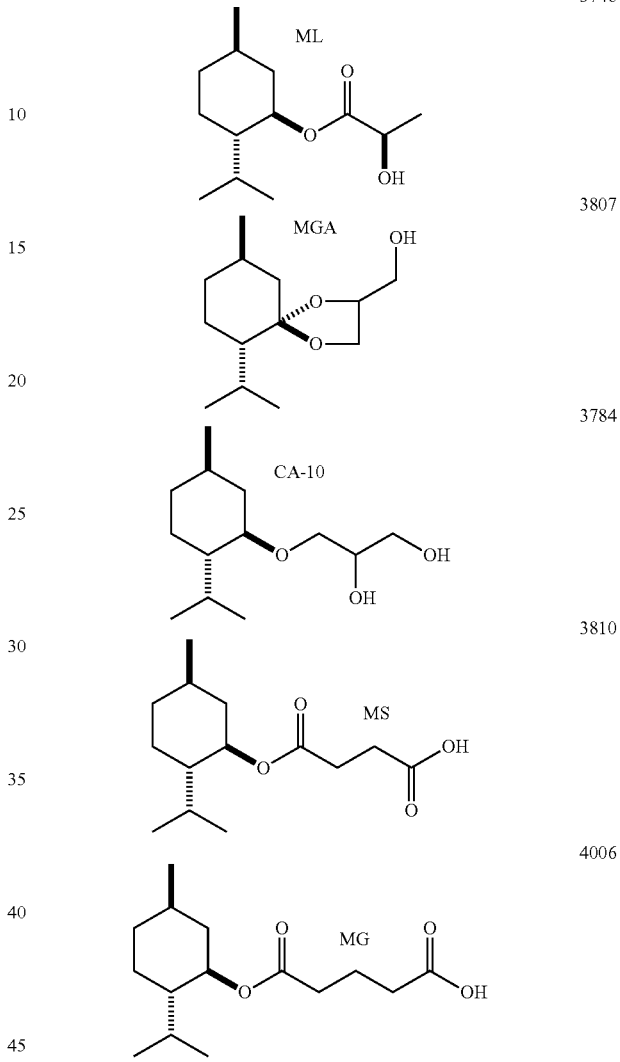

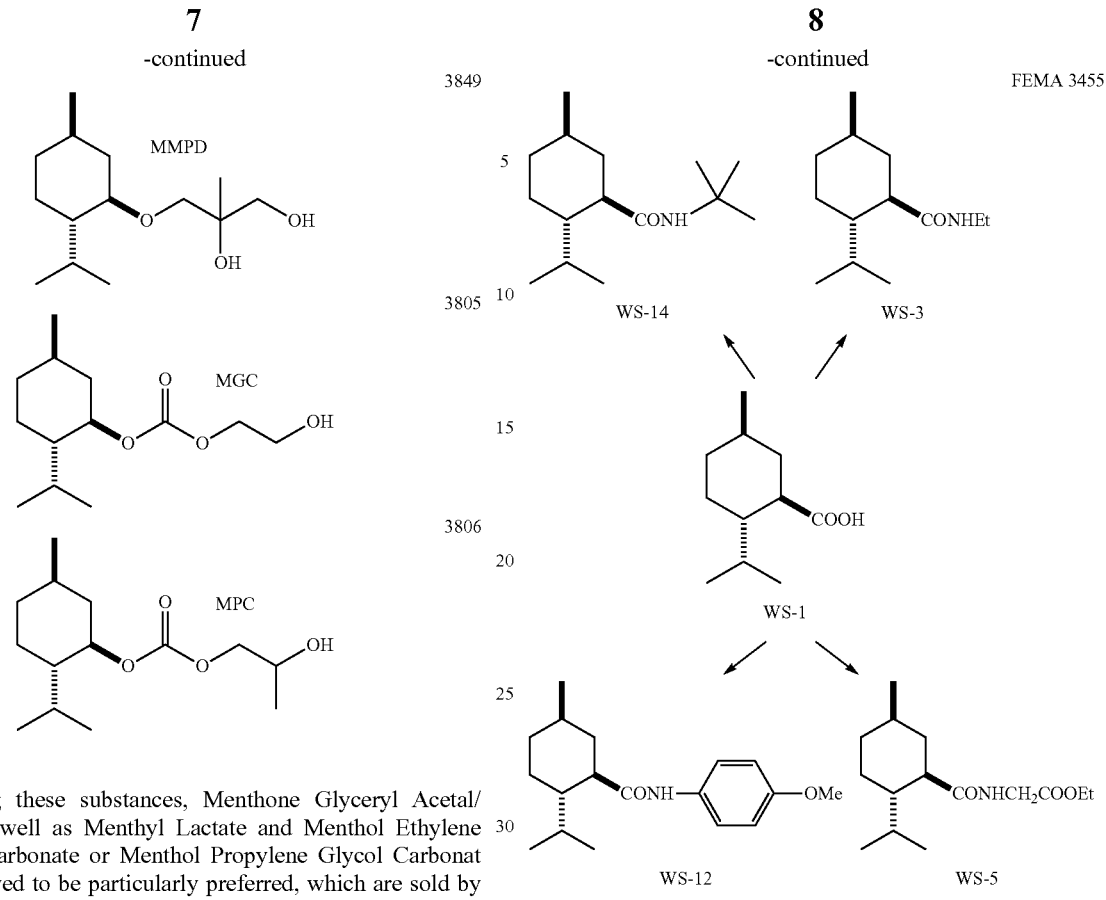

Among these substances, Menthone Glyceryl Acetal/Ketal as well as Menthyl Lactate and Menthol Ethylene Glycol Carbonate or Menthol Propylene Glycol Carbonat have proved to be particularly preferred, which are sold by the applicant under the designations Frescolat® MGA, Frescolat® ML, Frescolat® MGC and Frescolat® MPC.

In the 1970ies, menthol compounds having a C—C-bond at the 3' position were developed for the first time, a number of representatives of which can also be used within the meaning of the invention. These substances are generally referred to as WS types. The basic structure is a menthol derivative, where the hydroxyl group is replaced by a carboxyl group (WS-1). All other WS types derive from this structure such as, for example, the species WS-3, WS-4, WS-5, WS-12, WS-14 and WS-30 which are also preferred within the meaning of the invention. The two following diagrams show the synthesis pathways:

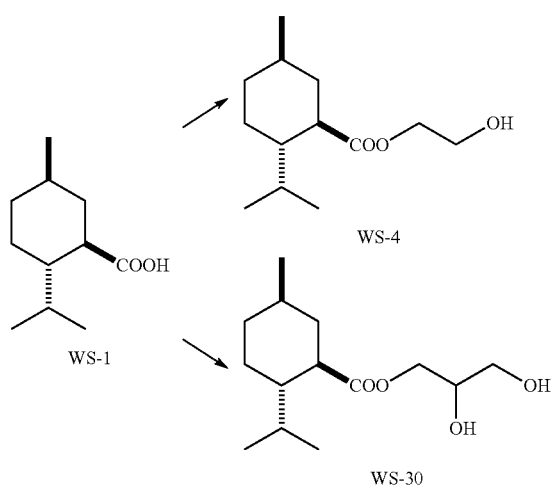

The esters that are derivable from WS-1 are described, for example, in U.S. Pat. No. 4,157,384, and the respective N-substituted amides in J. Soc. Cosmet. Chem. pp 185-200 (1978).

Not all cooling agents described above are solid at ambient temperature and may be formed to pastilles, or compacted. However, it is very well possible to introduce into the process mixtures of the solid and liquid cooling agents at ambient temperature and to obtain corresponding solid end products.

Preferred starting materials for carrying out the process according to the invention are melts of racemic menthol, particularly preferably of L-menthol, where the melted menthol may be of natural or synthetic origin and has an enantiomeric excess of typically at least 95, 96 or from 97 to 100%, preferably, 98, 98.5 or from 99 to 99.9%. Particularly suitable starting materials within the scope of the process according to the invention are also such melts of L-menthol which have a content of L-menthol of at least 95, 96 or 97 wt. % or above, preferably, from at least 98 to 100 wt. % and particularly preferably 98, 98.5 or from 99 to 99.9 wt. % (each based on the total weight of the melt) besides impurities such as, for example, residues of solvents, diastereomers of L-menthol or side products from synthesis or isolation processes.

Here, the term L-menthol melt is preferably understood to be such L-menthol which is mostly present, i.e., in amount of at least 80, or better 85 wt. %, preferably at least 90 or 95 wt. %, and particularly preferably at least 95, 96, 97, 98 or 99 wt. % in melted form, wherein the remaining weight proportions make up the amount of solid L-menthol in the melt. Herein, the proportion of solid menthol optionally contained in the melt may be such that it is still present in the melt due to a not completely finished melting process of the material used in the melt to provide the melt, or it is added to the completely or partly melted menthol in solid form, for example, in the form of crystals of L-menthol in the α-form. Such crystals of L-menthol in the α-form, which are also referred to as seed crystals, can also be obtained in a conventional approach, for example, by crystallisation of L-menthol from a solution or a melt containing L-menthol.

Within the scope of a preferred form of embodiment, such crystals of L-menthol in the α-form are used which are obtained by treating the L-menthol melt to be used according to the invention in a scraped-surface heat exchanger, as a result of which the seed crystals are formed in situ in the L-menthol melt that is to be solidified, avoiding an additional process step.

Ways of Carrying Out the Process

Within the meaning of the process according to the invention, a pre-scraped melt of a menthol compound is fed, for example, to a so-called Rotoform system by means of a pump.

In order to ensure a possibly complete congelation of the melts, preferably, of L-menthol in the α-form, seed crystals are added to the melt before feeding it to the Rotoformer and applying it onto the cooling belt, as described above. For example, this can be obtained by stirring previously comminuted crystals, for example, of the α-form of the L-menthol, into a feed vessel, or sprinkling them onto a used L-menthol melt (the liquid crystal film). Alternatively, it is possible to sprinkle α-menthol crystals onto the cooling belt. In a preferred embodiment of the invention, seeding is obtained by allowing the melt to pass through a heat exchanger that is operated below the melting point, where adhering crystallised material is scraped off the walls by a scraping means. The skilled person is familiar with such arrangements which are, for example, referred to as "scraped surface heat exchangers" and which are described in G. Arkenbout: "Melt Crystallization Technology", Technomic Publishing Co. 1995, p 230. Accordingly, a preferred embodiment of the process according to the invention is characterized in that the seed crystals are formed as a result of treating the melts to be used in a scraped surface heat exchanger.

A pre-scraped melt of menthol compounds which has a temperature in the range of from about 40 to about 60° C. and particularly of from about 43 to 50° C. and/or containing from about 0.1 to 12 wt. %, particularly from about 1 to about 5 wt. % seed crystals is preferably used. Particularly preferred is the use of a pre-scraped melt which contains from about 0.1 to 12 wt. % seed crystals of L-menthol. Also, menthol melts that have been undercooled to temperatures of from 42 to 43° C. can be used. In order to prevent cakings from forming in the scraped surface heat exchanger, which then peel off uncontrolledly, thus influencing the melting temperature, it is recommended to equip the heat exchanger with, for example, a trace heating.

In a particularly preferred embodiment of the invention, uniform drop deposition is performed by means of a so-called Rotoformer. The Rotoformer consists of a heated cylindrical internal body, which is supplied with liquid product, and an external tube that is equipped with numerous perforations, which concentrically rotates around the inner body, depositing drops of product on the whole length of a steel belt cooler in the process. A system of baffles and nozzles built into the internal body ensures an even pressure over the whole width of the component and thus a uniform exit of product through all perforations of the external tube. Here, all products, specifically the pastilles such obtainable, are of a uniform size from one edge of the steel belt to the other. The circumferential speed of the Rotoformer is preferably synchronous with the speed of the belt: therefore, the drops are deposited without deformation. The heat released during solidification and cooling is transferred from the stainless steel belt to the cooling water, which is sprayed against the underside of the belt. The water is collected in tanks and guided to the re-cooling system, at no stage it comes into contact with the product. After depositing the drop on the steel belt, a small amount of product will remain attached to the outer rims of the perforations of the external tube. A heatable refeed bar presses this product into an inner gap within the Rotoformer, from where it is mixed with original product and re-deposited onto the steel belt. To prevent the Rotoformer from plugging, for example, the use of a heat accumulation hood is recommended here. Corresponding combinations of Rotoformer and steel belt coolers are commercially available, for example, from the company Sandvik Process Systems GmbH, D-70736 Fellbach. A very similar technology is offered under the name Rollomat, for example, by the company Kaiser Process & Belt Technology GmbH, D-47800 Krefeld. Rotating and vibrating perforated plates are suitable, in principle, provided that the viscosity (according to the solids content in the melt) of the melt droplets is not too high.

Preferably, the melt drops are deposited by the Rotoformer onto a cooled belt, particularly, a cooled steel belt which may have a plurality of cooling zones, which can be tempered independently of one another, for example, to temperatures of below the melting or congelation point, which for L-menthol is in the range of from about 5 to about 42° C. Typical, for example, are cooling belts with three cooling zones of which the first two have temperatures of from about 25 to 30, and the last one of from about 15 to 20° C. For example, cooling belts are used which have a length of from about 2 to about 20 m and a width of from about 10 to about 200 cm. The speed of operation of the cooling belts is advantageously set such that, in consideration of the above mentioned geometry of the belts, a cooling time ensuring a complete crystallisation of the melts is maintained in this manner. Depending on the desired capacity, also larger units can of course be used, where the capacity is proportional to the width of the cooling belt and the duration time is a result of the length and the speed of the cooling belt. In principle, the process can also be performed on plants having a system capacity of from 50 to 1,000 kg/h or more.

Subsequently, the solid cooling agents are scraped from the belt, which is, for example, performed by means of a knife. In doing so, scraping can be performed either after the simple cooling period or with the aid of belt rewind after a further stay on the cooling belt close to the point of deposition. The material may stay longer on the belt to allow ripening and remain in an undertempered or post-tempered area.

Instead of a cooling belt, also disk pastillators or similar can be used, such as, for example, pastillating aids sold by the company Andritz Gouda, NL-2740 Waddingxveen.

The object of the process is to provide solid cooling agents that are crystallised as completely as possibly and which remain mechanically stable during storage. In doing so, it is to be considered that also the thermodynamically most stable form of L-menthol sublimes. As sublimation is a process at the surface of the particles, it is advantageous if the particles exhibit a small surface-to-volume ratio. The reason is that bridge connections between the particles are formed by sublimation during storage, which explains the caking. In addition, particles with partly curved surfaces are preferred, in which there are less contact points during pouring.

Within the scope of the present invention—as far as it relates to L-menthol as ingredient—the congelation or crystallisation of the L-menthol melt used is preferably considered completed if the contained L-menthol is present in solid form to at least about 80 wt. %, or better from 85 to 100 wt. %, preferably, from 90 to 100 wt. %, preferably, 95 or from 97 to 99.5 wt. %, and particularly preferably from 98 to 99 wt. % in the α-form. Such L-menthol exhibits changes only to a small extent by changing the material into the thermodynamically most stable form and thus changes with respect to its surface condition only to a small extent, if at all.

The particles according to the invention are characterised in that they contain only a low proportion of fines, exhibit a favourable surface/volume ratio and simultaneously have curved, but flat surfaces, which when poured result in contact areas that are as small as possible and that are resistant against abrasion, and, in addition, exhibit as few breaking edges as possible or none at all.

A further preferred subject-matter of the invention thus relates to menthol particles in the form of pastilles with a curved and a flat side, having a diameter of from about 1 to about 20 mm, preferably, 5 to 12 mm, and are furthermore characterized in that they (i) have a proportion of fines (i.e. a proportion of particles with an average diameter smaller than 1.6 mm) of less than 5 wt. %, preferably less than 2 wt. % and more preferably less than 1 wt. %, particularly preferably less than 0.5 wt. %, especially preferred less than 0.1 wt. %, and/or (ii) have an alpha-menthol content of at least 80 wt. %, preferably from about 85 to about 99 wt. % and particularly preferably from 90 to about 95 wt. %; and/or (iii) have a surface-to-volume ratio of less than 2:1/mm, preferably less than 1.5:1/mm and particularly preferably less than 1.0:1/mm.

(iv) have curved surfaces so that the ratio of plane surface to the total surface of the particle is 60% maximum, preferably less than 50%, and more preferably less than %.

The form of the obtained solidified L-menthol present in each case and thus the completion of the congelation process can be determined by processes known to the skilled person such as x-ray diffraction or powder diffractometry (see, for example, Joel Bernstein, "Polymorphism in Molecular Crystals", Oxford University Press 2002, pp 94-150).

INDUSTRIAL APPLICABILITY

A further subject-matter of the invention relates to cooling agents in solid form which are obtainable according to the process described above and present in the form of flakes or, preferably, pastilles. By means of the process according to the invention, for example, the production of pastilles with diameters of from about 1 to about 20 mm, preferably from about 5 to about 12 mm, this is possible without any problem. As the particles are also to be brought into solution after storage, the particle size indicated is an optimum balance between solubility on the one hand and an inclination to cake on the other.

These cooling agents also, preferably, share the property that they (i) have a proportion of fines (i.e., a portion of particles with an average diameter of less than 1.6 mm) of less than 5 wt. %, preferably less than 2 wt. % and more preferably less than 1 wt. %, particularly preferably less than 0.5 wt. %, especially preferred less than 0.1 wt. %, and/or (ii) have an alpha-menthol content of at least 80 wt. %, preferably from about 85 to about 99 wt. % and particularly preferably from about 90 to about 95 wt. %; and/or (iii) have a surface-to-volume ratio of less than 2:1/mm, preferably less than 1.5:1/mm and particularly preferably less than 1.0:1/mm.

(iv) have curved surfaces, so that the ratio of plane surface to the total surface of the particle is 60% maximum, preferably less than 50% and more preferably less than 40%.

A last subject-matter of the present invention is the use of the solid cooling agents or the menthol particles in cosmetic or pharmaceutical preparations and foods.

EXAMPLES

Examples of Production

In the following examples of embodiment it was intended to determine how the production of pastilles with an optimum surface-to-volume ratio and good caking properties are to be produced and examined. Also, it was intended to determine process conditions ensuring the production of completely crystallised material. Any post-crystallisation in the packaged state should be avoided.

Test Set Up and Performance of the Process

Figure 6:
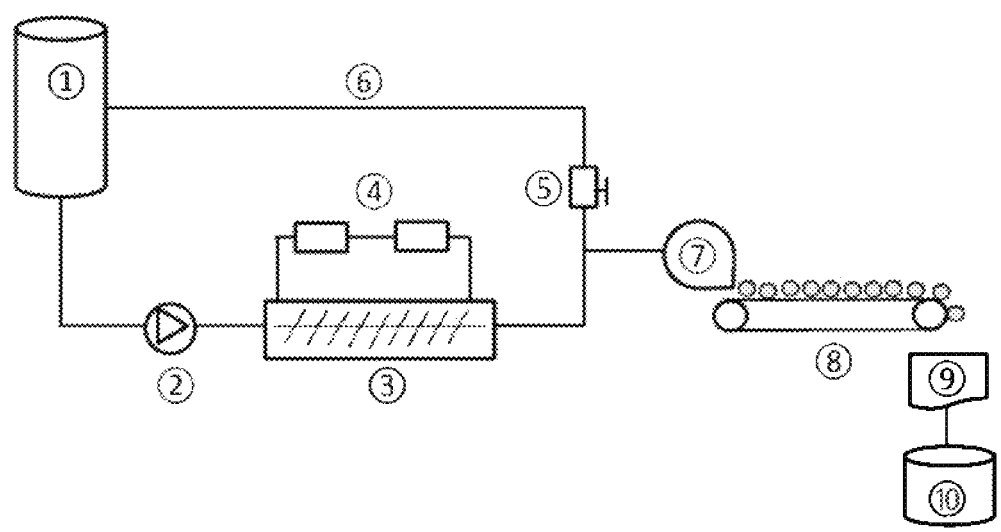

The tests were performed on a steel belt cooler with a Rotoformer and an upstream scraped surface heat exchanger as schematically illustrated in FIG. 6. Here, the reference signs mean the following:

| | |
|---|---|
| 1 | Educt container |
| 2 | Educt pump |
| 3 | Extruder |
| 4 | Heat exchanger |
| 5 | Valve |
| 6 | Re-feeding of educt |
| 7 | Rotoformer |
| 8 | Cooling belt with three cooling zones T1, T2, T3 |
| 9 | Granulator |
| 10 | Product deposition |

In doing so, a melt that has been pre-scraped in the scraped surface heat exchanger (i.e., a suspension of seed crystals in menthol) was deposited onto a pre-cooled steel belt by means of a Rotoformer. The length of the cooling belt was 12.5 m, the width of the belt was 600 mm. The cooling belt had three cooling zones which could be tempered independently of one another. Scraping from the cooling belt was performed by knife, either after a single cooling period or with the aid of of the belt rewind near the deposition location. In doing so, the material was subjected to additional cooling on the 12.5 m of the belt rewind. The speed of operation of the cooling belt (and thus the capacity of the cooling belt) was changed only insignificantly in the course of the tests, as a result of which an output in the range of from 150-165 kg/h during the tests was obtained. The material obtained was separated from attached fines by means of a vibrating screen (company Allgaier; sieve hole width: 1.6 mm and 1.25 mm). The deposition temperature of the material was determined by measurement in a Dewar vessel using a thermocouple element. The change of temperature after scraping from the belt will in the following be referred to as post-crystallisation heat. Output was determined with a stopwatch and a scale at the middle part of a test run. For each test, about 20 to 30 kg pastilles were removed as initial forerunnings. The materials obtained were packed into F1 cardboard boxes with a PE inner bag—(Symrise standard packaging means for compacted menthol) during the test.

Example 1

A starting temperature of 30° C. was selected for T1 and T2, as this temperature of the metal belt is near the congelation temperature of the α-form (see FIG. 1) and only a small amount of γ-form could be expected at a superposed spontaneous crystallisation. The congelation temperature in the pastille should be higher as a result of an inferior heat transfer through the congealed menthol and should thus, preferably, lead to the formation of the α-form. At T3, 15° C. were selected to increase the heat transfer through the already solidified menthol thus ensuring a complete crystallisation. The test conditions are reflected in Table 1.

TABLE 1

Test conditions

| | |
|---|---|
| Temperature zones of the cooling belt | T1: 30° C.; T2: 30° C.; T3: 15° C. |
| Temperature of the scraped surface heat exchanger | 41.5° C. |
| Output | 150 kg/h |
| Weights (cardboard boxes) | 15.6 kg/12.45 kg/19.50 kg/21.05 kg/20.6 kg |
| Fines | 41.8 g per 89.2 kg (469 g/t pastilles) |
| Deposition temperature | 25.2° C. |
| Post-crystallisation heat | 1° C. over 1 h Room temperature: 27° C. |

After removing small forerunnings, pure white pastilles were obtained (FIG. 1). The pastilles were completely crystallised and difficult to split with a spatula/knife.

Example 2

Figure 2:
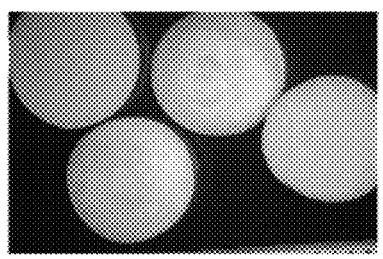
FIG. 2 is a photograph of pastilles prepared according to Example 2 of the present invention.

After passing the cooling belt, the pastilles were not completely crystallised at T2. At the end of the cooling belt at T3, the pastilles were slightly soft at the upper end and easily splittable with a knife. The test conditions are reflected in Table 2; the pastilles are shown in FIG. 2.

TABLE 2

Test conditions

| | |
|---|---|
| Temperature zones of the cooling belt | T1: 30° C.; T2: 30° C.; T3: 18° C. |
| Temperature of the scraped surface heat exchanger | 41.4-41.6° C. |
| Output | 165 kg/h |
| Weights (cardboard boxes) | 19.82 kg/20.48 kg/20.93 kg/20.27 kg |
| Fines | 106.4 g per 81.5 kg (1305 g/t pastilles) |
| Deposition temperature | 24.4° C. |
| Post-crystallisation heat | 1° C. over 30 min Room temperature: 27° C. |

Example 3

Figure 3:
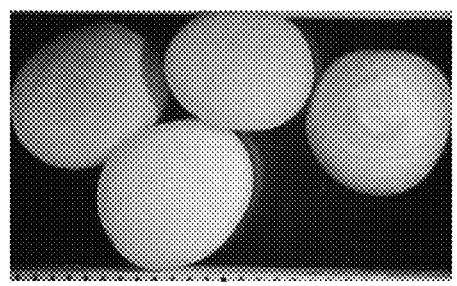
FIG. 3 is a photograph of pastilles prepared according to Example 3 of the present invention.

In the course of test 3, the scraper knife at the end of the cooling belt was removed. The belt rewind was used as an additional post-cooling section. The pastilles were hard and fully crystallised after scraping. The test conditions are reflected in Table 3; the pastilles are shown in FIG. 3.

TABLE 3

Test conditions

| | |
|---|---|
| Temperature zones of the cooling belt | T1: 30° C.; T2: 30° C.; T3: 18° C.; belt rewind post-cooling |
| Temperature of the scraped surface heat exchanger | 41.4-41.6° C. |
| Output | 165 kg/h |
| Weights (cardboard boxes) | 20.57 kg/20.49 kg/19.36 kg |
| Fines | 48.6 g per 60.42 kg (804 g/t pastilles) |
| Deposition temperature | 24.4° C. |
| Post-crystallisation heat | 1° C. over 30 min Room temperature: 27° C. |

Example 4

Figure 4:
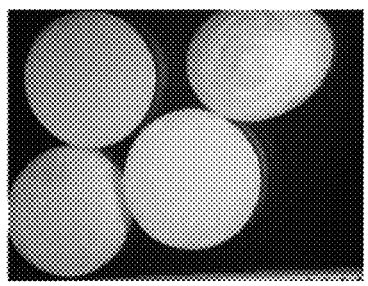
FIG. 4 is a photograph of pastilles prepared according to Example 4 of the present invention.

The pastilles were comparable to example 1. The test conditions are reflected in Table 4; the pastilles are shown in FIG. 4.

TABLE 4

Test conditions

| | |
|---|---|
| Temperature zones of the cooling belt | T1: 30° C.; T2: 30° C.; T3: 15° C. |
| Temperature of the scraped surface heat exchanger | 41.5-41.6° C. |
| Output | 150 kg/h |
| Weights (cardboard boxes) | 18.85 kg/18.75 kg/19.45 kg/19.65 kg |
| Fines | 106.1 g per 76.7 kg (1383 g/t pastilles) |
| Deposition temperature | 25.2° C. |
| Post-crystallisation heat | 1.0° C. over 30 min Room temperature: 28° C. |

Example 5

Figure 5:
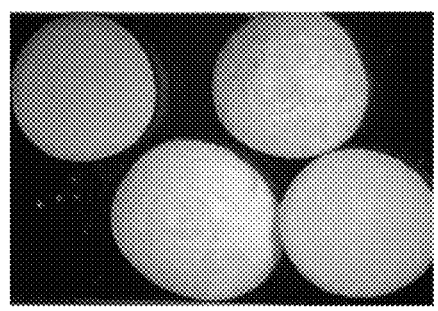
FIG. 5 is a photograph of pastilles prepared according to Example 5 of the present invention, and
FIG. 6 schematically illustrates a steel belt cooler with a Rotoformer and an upstream scraped surface heat exchanger for producing the pastilles of the examples according to the present invention.

In the course of example 5, the scraper knife at the end of the cooling belt was removed. The belt rewind was used as an additional post-cooling section. The pastilles were hard and fully crystallised after scraping. The test conditions are reflected in Table 5; the pastilles are shown in FIG. 5.

TABLE 5

Test conditions

| | |
|---|---|
| Temperature zones of the cooling belt | T1: 30° C.; T2: 30° C.; T3: 15° C.; belt rewind post-cooling |
| Temperature of the scraped surface heat exchanger | 41.4-41.6° C. |
| Output | 165 kg/h |
| Weights (Kartons) | 15.4 kg |
| Deposition temperature | 22.2° C. |
| Post-crystallisation heat | 1.0° C. over 30 min Room temperature: 28° C. |

Example 6

Comparison Example V1

Example 1 was repeated, cooling, however, was performed by means of a double belt cooler with cooled steel surfaces and a gap width of 0.3 cm (length 12 m, width 35 cm). The double belt cooler also had 3 cooling zones (30° C., 30° C., 15° C.); the product was scraped off in the form of flakes by means of a knife.

5 kg each of the pastilles of example 1 according to the invention (diameter: 5 mm) and of the comparison example V1 were filled into bags of synthetic material which were stored in cardboard boxes at 20° C. for a period of 6 weeks. The results are summarised in Table 6.

TABLE 6

Storage tests

| Storage time | Example 1 | Comparison example V1 |
| --- | --- | --- |
| 1 week | Material easily separable at the surface. No agglomeration. | Material easily separable at the surface. No agglomeration. |
| 2 weeks | Material easily separable at the surface. In the centre of the filling, a small amount cakes to form agglomerations which are manually separable. | Material separable at the surface. In the centre of the filling there are agglomerations which are separable by means of a shovel. |
| 3 weeks | Material easily separable at the surface. In the centre of the filling, a small amount cakes to form agglomerations which are manually separable. | Material separable at the surface. In the centre of the filling there are distinct agglomerations which are separable by means of a shovel. |
| 4 weeks | Material easily separable at the surface. In the centre of the filling, a small amount cakes to form agglomerations which are manually separable. | Material is separable at the surface. In the centre of the filling there are distinct agglomerations which are separable by means of a shovel. |
| 5 weeks | Material is separable at the surface. In the centre of the filling there are agglomerations which are separable by means of a shovel. | Material difficult to separate at the surface. In the centre of the filling there are distinct agglomerations, which are separable by means of a shovel. At the surface, slight formation of needles due to sublimation. |
| 6 weeks | Material is separable at the surface. In the centre of the filling there are distinct agglomerations, which are separable by means of a shovel. At the surface, slight formation of needles due to sublimation. | 80% is agglomerated, distinct formation of needles due to sublimation. |

Example 7

In order to prove that the crystal form alone is not decisive for the inclination to cake, 20 kg of 8 L-menthol that had been stored for 8 months and which was completely present in its α-form, were comminuted by means of a seave mill with a 3 mm sieve hole insert to obtain crystal powder. In doing so, no increase in temperature as a result of the comminution process was measured. Subsequently, the crystal powder was stored again. Already after two weeks the powder was caked, forming a block which could only be loosened locally by heavy kneading.

The invention claimed is:

1. A process for the production of a menthol pastille with a curved side and a flat side, comprising the step of:
    placing a pre-scraped melt of menthol compounds with added seed crystals of L-menthol onto a pre-cooled single steel belt by even deposition of drops, and wherein the steel belt has cooling zones independently of one another each having a temperature below the respective melting point of said L-menthol seed crystals in the range of from about 15 to about 42° C.

2. The process of claim 1, wherein seed crystals are used which were formed by treatment of the melt to be used in a scraped surface heat exchanger.

3. The process of claim 1, wherein the menthol compounds are selected from the group consisting of Menthol, Racemic Menthol, Menthol Methyl Ether, Menthone Glyceryl Acetal (FEMA GRAS 3807), Menthone Glyceryl Ketal (FEMA GRAS 3808), Menthyl Lactate (FEMA GRAS 3748), Menthol Ethylene Glycol Carbonate (FEMA GRAS 3805), Menthol Propylene Glycol Carbonate (FEMA GRAS 3806), Menthyl-N-ethyloxamate, Monomethyl Succinate (FEMA GRAS 3810), Monomenthyl Glutamate (FEMA GRAS 4006), Menthoxy-1,2-propanediol (FEMA GRAS 3784), Menthoxy-2-methyl-1,2-propanediol (FEMA GRAS 3849) and the menthane carboxylic acid esters and amides WS-3, WS-4, WS-5, WS-12, WS-14 and WS-30 and mixtures thereof.

4. The process of claim 1, wherein the pre-scraped melt of menthol compounds has a temperature in the range of from about 40 to about 60° C.

5. The process of claim 1, wherein the pre-scraped melt contains from about 0.1 to 12 wt. % seed crystals.

6. The process of claim 5, wherein the pre-scraped melt contains from about 0.1 to about 12 wt. % seed crystals of L-menthol.

7. The process of claim 1, wherein the step of placing a pre-scraped melt of menthol compounds with added seed crystals of L-menthol onto a pre-cooled single steel belt occurs by even deposition of drops from a rotoformer.

\* \* \* \* \*